(12) United States Patent
Martin et al.

(10) Patent No.: US 6,969,533 B1
(45) Date of Patent: Nov. 29, 2005

(54) BEVERAGE AND ADDITIVE FOR INFLAMED TISSUE

(76) Inventors: Kenneth A. Martin, 8907 Kanis Rd., Suite 330, Little Rock, AR (US) 72205; Teresa Leigh Barr, P.O. Box 1500, Port Townsend, WA (US) 98368

( * ) Notice: Subject to any disclaimer, the term of this patent is extended or adjusted under 35 U.S.C. 154(b) by 90 days.

(21) Appl. No.: 10/630,569

(22) Filed: Jul. 30, 2003

Related U.S. Application Data

(63) Continuation-in-part of application No. 10/241,542, filed on Sep. 11, 2002, now Pat. No. 6,660,308.

(51) Int. Cl.$^7$ .............................................. A61K 35/78
(52) U.S. Cl. ..................... 424/728; 514/62; 514/356; 514/709; 426/590
(58) Field of Search .................... 424/728; 514/62, 514/356, 709; 426/590

(56) References Cited

U.S. PATENT DOCUMENTS

| | | |
|---|---|---|
| 3,686,406 A | 8/1972 | Sherlock |
| 4,616,039 A | 10/1986 | Herschler |
| 4,621,137 A | 11/1986 | Miyake et al. |
| 4,647,453 A * | 3/1987 | Meisner |
| 5,827,834 A | 10/1998 | Falk et al. |
| 5,852,002 A | 12/1998 | Falk et al. |
| 5,916,565 A | 6/1999 | Rose et al. |
| 5,929,048 A | 7/1999 | Falk et al. |
| 5,932,560 A | 8/1999 | Falk et al. |
| 6,194,392 B1 | 2/2001 | Falk et al. |
| 6,358,526 B1 | 3/2002 | Mergen et al. |
| 6,399,093 B1 | 6/2002 | Petrus |
| 6,660,308 B1 * | 12/2003 | Martin et al. |

* cited by examiner

*Primary Examiner*—Susan D. Coe
(74) *Attorney, Agent, or Firm*—Buskop Law Group, P.C.; Wendy Buskop

(57) ABSTRACT

The invention is a beverage involving an ingestible fluid and a dosage amount of an ingestible composition for treating an inflammatory tissue in a mammal, involving the inflammatory tissue selected from the group comprising underperfused tissue, inflamed joints, inflamed muscles, wherein the dosage amount has a glucose ingredient, such as glucosamine sulfate, glucosamine hydrochloride, n-acetyl glucosamine, and combinations thereof; a chondroitin component, such as chondroitin sulfate, chondroitin hydrochloride, and combinations thereof; a member of the family of araliaceae for buffering the ingestion of the glucose ingredient, such as American ginseng, Siberian ginseng, panax ginseng, and combinations thereof; a calcium containing component; and a sulfonate having at least one methyl group ingesting the beverage.

21 Claims, No Drawings

BEVERAGE AND ADDITIVE FOR INFLAMED TISSUE

This application is a continuation-in-part of U.S. patent application Ser. No. 10/241,542 filed Sep. 11, 2002, now U.S. Pat. No. 6,660,308 and claims priority from same. U.S. patent application Ser. No. 10/241,542 is hereby incorporated by reference.

FIELD OF THE INVENTION

The present invention is a beverage used to treat an inflammatory tissue or arthritic condition in a mammal involving tissue that is underperfused tissue, inflamed joints, or inflamed muscles. The present invention is also a beverage additive in which those who suffer from inflammatory tissues or arthritic conditions can easily receive their daily dosage to ease their pain.

BACKGROUND OF THE INVENTION

A need has existed for a large convenient dosage, that is not in a solid form, of glucose, chondroitin, a member of the family of araliaceae, and a calcium containing component to be taken in one daily dose that can be quickly absorbed into the bloodstream, thereby bypassing the gut and eliminating the adverse reactions to the elemental ingredients, as well as protecting and buffering the lining of the stomach from the high dosages of the ingredients. The one daily dose also needs to buffer the glucose levels in the blood, thereby significantly reducing or eliminating the adverse effects of the essential ingredients. This makes it possible to administer a one time daily large dose that is fast-absorbing, using a powerful vasodilatation system, is tasteless in most liquids, odorless, non-steroidal, and has no adverse symptoms of nausea, heartburn, diarrhea, constipation or headache. The daily dose needs to perfuse underperfused tissue by saturating the tissue, increasing mobility of a mammal in all directions, decreasing inflammation, maintaining cartilage viability, and increasing strength, muscle flexibility and endurance. The daily dose also needs to be cost effective and capable of mass production.

Petrus U.S. Pat. No. 6,399,093 discloses a method and composition for the treatment of musculoskeletal disorders in mammals by the application of a topical composition comprising a permeation enhancing amount of one or more penetration enhancers, and one or more bio-affecting agents to provide anti-inflammatory relief and analgesia to the applied body part.

Falk U.S. Pat. Nos. 5,827,834; 5,852,002; 5,929,048; and 5,932,560 refer to methods of using MSM, hyaluronic acid, and glucosamine to reduce the swelling of brain tumors in a similar manner as Falk U.S. Pat. No. 6,194,392.

The present invention has been designed to be beneficial because it is fast-absorbing, tasteless, odorless, non-steroidal, and a vasodilator. The invention additive also is a one-time daily large dose. There are no symptoms of nausea, heartburn, constipation, diarrhea, and headaches associated with the present invention. In addition, the present invention contains a high quantity of glucose and a high quantity of chondroitin.

The beverage of the present invention is also cost effective since it is capable of being mass-produced. An eight ounce or twelve ounce beverage can contain the single serving daily dose.

The present invention is also beneficial because it perfuses underperfused tissues. This means the additive saturates the tissue, increases mobility in all directions, decreases inflammation, maintains cartilage viability, increases strength, increases muscle flexibility, and increases endurance.

SUMMARY OF THE INVENTION

The invention relates to a beverage that is an ingestible fluid and a dosage amount of an ingestible composition. The ingestible composition is a composition for treating an inflammatory tissue in a mammal, such as underperfused tissue, inflamed joints, inflamed muscles. The dosage composition includes a glucose ingredient, such as glucosamine sulfate, glucosamine hydrochloride, n-acetyl glucosamine, and combinations thereof; a chondroitin component, such as chondroitin sulfate, chondroitin hydrochloride, and combinations thereof; a member of the family of araliaceae; calcium containing component; and a sulfonate having at least one methyl group ingesting the beverage. The family of araliaceae is used for buffering the ingestion of the glucose ingredient. The araliaceae is a member of the ginseng group, such as American ginseng, Siberian ginseng, panax ginseng, and combinations thereof.

DETAILED DESCRIPTION OF THE PREFERRED EMBODIMENT

Before explaining the present invention in detail, it is to be understood that the invention is not limited to the particular embodiments and that it can be practiced or carried out in various ways.

The invention is a beverage made of an ingestible fluid and a dosage amount of an ingestible composition for treating an inflammatory tissue or arthritic condition in a mammal involving tissue that is underperfused tissue, inflamed joints, or inflamed muscle.

The dosage amount of the beverage is made from a glucose component such as a glucosamine sulfate, a glucosamine hydrochloride, an n-acetyl glucosamine, and combinations thereof.

The dosage amount of the beverage includes a chondroitin component such as a chondroitin sulfate, a chondroitin hydrochloride, and combinations thereof.

The dosage amount of the beverage includes a member of the family of araliaceae for buffering the ingestion of the glucose ingredient, such as American ginseng, Siberian ginseng, panax ginseng, and combinations thereof.

The dosage amount of the beverage further includes a calcium containing component. The calcium containing component can include calcium carbonate, calcium citrate, coral calcium, or combinations thereof. The dosage amount of the calcium component can include from about 10 mg to about 1000 mg.

The dosage amount of the beverage further includes a sulfonate having at least one methyl group. The preferred dosage is between 10 mg and 3000 mg. The preferred sulfonate with at least one methyl group is methyl sulfonyl methane (MSM).

The beverage can further include a lubricating sodium agent.

In the beverage, the invention contemplates variations in the dosage amounts. A preferred dosage amount is 1000 mg to 2000 mg of a glucose ingredient, 10 mg to 1500 mg of a chondroitin component, 5 mg to 800 mg of a member of the family of araliaceae, 10 mg to 1500 mg of a calcium containing component, and 10 mg to 3000 mg of the sulfonate with at least one methyl group.

The dosage amount of the beverage can further include from about 10 mg to about 3000 mg of Vitamin C.

The dosage amount of the beverage can further include from about 10 mg to about 20 mg of Vitamin $B_3$. Examples of $B_3$ Vitamins contemplated in the beverage are a vasodialating niacin, a vasodialating niacinamide, and combinations thereof.

The fluid in the ingestible fluid of the beverage can be water, coffee, tea, artificial drinks, alcoholic fluids, non-alcoholic fluids, fruit juice, vegetable juice, blends of juice, juice and water blends, concentrates of juice, soda, sports drinks, and combinations thereof. The invention contemplates that any fluid normally ingested by people is acceptable for the beverage.

The invention is a method for treating an inflammatory tissue that is underperfused tissue, inflamed joints, or inflamed muscle, the method consists of ingesting a beverage made of an ingestible fluid and a dosage amount of an ingestible composition. The method ends by ingesting the beverage.

The glucose component in the method can be a glucosamine sulfate, a glucosamine hydrochloride, an n-acetyl glucosamine, and combinations thereof. The chondroitin component can be a chondroitin sulfate, a chondroitin hydrochloride, and combinations thereof.

The member of the family of araliaceae is used for buffering the ingestion of the glucose ingredient. The preferred member of the family of araliaceae is ginseng. Types of ginseng contemplated by the method include as American ginseng, Siberian ginseng, panax ginseng, and combinations thereof.

The method of providing a beverage comprises using a calcium containing component, such as calcium carbonate, calcium citrate, coral calcium, or combinations thereof. The preferred dosage of the calcium containing component is between about 10 mg and about 1000 mg.

The method of providing the beverage can include the step of using a dosage amount of 1000 mg to 2000 mg of a glucose ingredient, 10 mg to 1500 mg of a chondroitin component, 5 mg to 800 mg of a member of the family of araliaceae, 10 mg to 1500 mg of a calcium containing component, and 10 mg to 3000 mg of the sulfonate with at least one methyl group.

The method can include using from about 10 mg to about 3000 mg of Vitamin C.

The method of providing the beverage can include using from about 10 mg to about 20 of a Vitamin $B_3$, such as a vasodialating niacin, vasodialating niacinamide, and combinations thereof.

The method of providing the beverage can include using a member of an ingestible fluid selected from the group consisting of water, coffee, tea, artificial drinks, alcoholic fluids, non-alcoholic fluids, fruit juice, vegetable juice, blends of juice, juice and water blends, concentrates of juice, soda, sports drinks, and combinations thereof.

While this invention has been described with emphasis on the preferred embodiments, it should be understood that within the scope of the appended claims, the invention might be practiced other than as specifically described herein.

What is claimed is:

1. A beverage comprising:
   a. an ingestible fluid; and
   b. a dosage amount of an ingestible composition for treating an inflammatory tissue in a mammal, involving the inflammatory tissue selected from the group comprising underperfused tissue, inflamed joints, inflamed muscles, and wherein the dosage amount comprises:
      i. a glucose ingredient selected from the group consisting of glucosamine sulfate, glucosamine hydrochloride, n-acetyl glucosamine, and combinations thereof;
      ii. a chondroitin component selected from the group consisting of chondroitin sulfate, chondroitin hydrochloride, and combinations thereof;
      iii. a member of the family of araliaceae for buffering the ingestion of the glucose ingredient; and the member is a ginseng selected from the group consisting of American ginseng, Siberian ginseng, panax ginseng, and combinations thereof;
      iv. a calcium containing component; and
      v. a sulfonate having at least one methyl group.

2. The beverage of claim 1, wherein the calcium containing component is selected from the group consisting of calcium carbonate, calcium citrate, coral calcium, or combinations thereof.

3. The beverage of claim 1, wherein the calcium containing component ranges from about 10 mg to about 1000 mg.

4. The beverage of claim 1, further comprising a lubricating sodium agent.

5. The beverage of claim 1, wherein the dosage amount comprises;
   a. 1000 mg to 2000 mg of a glucose ingredient;
   b. 10 mg to 1500 mg of a chondroitin component;
   c. 5 mg to 800 mg of a member of the family of araliaceae;
   d. 10 mg to 1500 mg of a calcium containing component; and
   e. 10 mg to 3000 mg of a sulfonate having at least one methyl group.

6. The beverage of claim 5, further comprising from about 10 mg to about 3000 mg of Vitamin C.

7. The beverage of claim 5, further comprising from about 10 mg to about 20 mg of Vitamin $B_3$.

8. The beverage of claim 7, wherein the Vitamin $B_3$ is selected from the group consisting of vasodialating niacin, vasodialating niacinamide, and combinations thereof.

9. The beverage of claim 5, wherein the ingestible fluid is a member selected from the group consisting of: water, coffee, tea, artificial drinks, alcoholic fluids, non-alcoholic fluids, fruit juice, vegetable juice, blends of juice, juice and water blends, concentrates of juice, soda, sports drinks, and combinations thereof.

10. The beverage of claim 5, wherein the sulfonate is methyl sulfonyl methane (MSM).

11. A method for treating inflamed tissue comprising:
   a. providing a beverage, wherein the beverage comprises
      i. an ingestible fluid; and
      ii. a dosage amount of an ingestible composition for treating an inflammatory tissue in a mammal, involving the inflammatory tissue selected from the group comprising underperfused tissue, inflamed joints, inflamed muscles, and wherein the dosage amount comprises:
         1. a glucose ingredient selected from the group consisting of glucosamine sulfate, glucosamine hydrochloride, n-acetyl glucosamine, and combinations thereof;
         2. a chondroitin component selected from the group consisting of chondroitin sulfate, chondroitin hydrochloride, and combinations thereof;
         3. a member of the family of araliaceae for buffering the ingestion of the glucose ingredient; and the member is a ginseng selected from the group consisting of American ginseng, Siberian ginseng, panax ginseng, and combinations thereof;

4. a calcium containing component; and 5. a sulfonate having at least one methyl group;

b. ingesting the beverage.

12. The method of claim 11, wherein the step of providing the beverage comprises using a calcium containing component selected from the group consisting of calcium carbonate, calcium citrate, coral calcium, or combinations thereof.

13. The method of claim 11, wherein the step of providing the beverage using a dosage of the calcium containing component ranges from about 10 mg to about 1000 mg.

14. The method of claim 11, wherein the step of providing the beverage further comprises using a lubricating sodium agent.

15. The method of claim 11, wherein the step of providing the beverage comprises the step of using a dosage amount of:

a. 1000 mg to 2000 mg of a glucose ingredient;

b. 10 mg to 1500 mg of a chondroitin component;

c. 5 mg to 800 mg of a member of the family of araliaceae;

d. 10 mg to 1500 mg of a calcium containing component; and e. 10 mg to 3000 mg of a sulfonate having at least one methyl group.

16. The method of claim 15, further comprising the step of using from about 10 mrg to about 3000 mg of Vitamin C.

17. The method of claim 15, further comprising from about 10 mg to about 20 mg of Vitamin $B_3$.

18. The method of claim 17, wherein the Vitamin $B_3$ is selected from the group consisting of vasodialating niacin, vasodialating niacinamide, and combinations thereof.

19. The method of claim 15, wherein the step of providing the beverage comprises using a Vitamin 13 selected from the group consisting of vasodialating niacin, vasodialating niacinamide, and combinations thereof.

20. The method of claim 15, wherein the step of providing the beverage comprises using a member of an ingestible fluid selected from the group consisting of water, coffee, tea, artificial drinks, alcoholic fluids, non-alcoholic fluids, fruit juice, vegetable juice, blends of juice, juice and water blends, concentrates of juice, soda, sports drinks, and combinations thereof.

21. The method of claim 15, wherein the step of using the sulfonate is using methyl sulfonyl methane (MSM).

* * * * *